(12) United States Patent
Ando et al.

(10) Patent No.: US 7,729,565 B2
(45) Date of Patent: Jun. 1, 2010

(54) FIBER SENSOR AND FIBER SENSOR DEVICE

(75) Inventors: Takayuki Ando, Tokyo (JP); Hisashi Koaizawa, Tokyo (JP); Takashi Shigematu, Tokyo (JP); Ken Tsukii, Tokyo (JP); Masaki Izumo, Tokyo (JP)

(73) Assignee: The Furukawa Electric Co., Ltd. (JP)

( * ) Notice: Subject to any disclaimer, the term of this patent is extended or adjusted under 35 U.S.C. 154(b) by 0 days.

(21) Appl. No.: 11/791,583

(22) PCT Filed: Nov. 25, 2005

(86) PCT No.: PCT/JP2005/021726

§ 371 (c)(1),
(2), (4) Date: Jan. 4, 2008

(87) PCT Pub. No.: WO2006/057358

PCT Pub. Date: Jan. 6, 2006

(65) Prior Publication Data

US 2008/0093541 A1    Apr. 24, 2008

(30) Foreign Application Priority Data

Nov. 25, 2004    (JP) .............................. 2004-339774

(51) Int. Cl.
*G02B 6/00* (2006.01)
(52) U.S. Cl. .............................. 385/12; 385/88; 385/89; 356/246
(58) Field of Classification Search .................. 385/12, 385/88–92; 250/227.11; 356/246, 445
See application file for complete search history.

(56) References Cited

U.S. PATENT DOCUMENTS

| 5,164,589 | A  | * | 11/1992 | Sjodin | .................... 250/227.24 |
| 6,194,900 | B1 | * | 2/2001  | Freeman et al. | ............. 324/321 |
| 6,438,279 | B1 | * | 8/2002  | Craighead et al. | ............. 385/12 |
| 6,882,420 | B2 | * | 4/2005  | Rassman et al. | ............ 356/369 |
| 7,058,244 | B2 | * | 6/2006  | Iida et al. | ....................... 385/12 |
| 7,145,146 | B2 | * | 12/2006 | Ogawa et al. | .......... 250/339.07 |
| 2002/0031838 | A1 | * | 3/2002 | Meinhart et al. | ............ 436/514 |

(Continued)

FOREIGN PATENT DOCUMENTS

JP        2000-39401        2/2000

(Continued)

OTHER PUBLICATIONS

International Search Report for International Application No. PCT/JP2005/021726 mailed Dec. 20, 2005.

(Continued)

*Primary Examiner*—Ellen Kim
(74) *Attorney, Agent, or Firm*—Cantor Colburn LLP

(57) ABSTRACT

A fiber sensor comprising: an optical waveguide unit having a measurement surface formed at an end of an optical waveguide; and a channel unit through which a specimen, serving as a measurement object to be measured by contact with the measurement surface, is caused to flow in and out via a specimen channel, wherein the optical waveguide is fixed to the optical waveguide unit such that the measurement surface forms a part of a channel wall surface of the channel unit, and the optical waveguide unit is provided so as to be detachable from the channel unit.

16 Claims, 8 Drawing Sheets

U.S. PATENT DOCUMENTS

| | | | |
|---|---|---|---|
| 2003/0017079 A1* | 1/2003 | Hahn et al. | 422/82.09 |
| 2005/0136685 A1* | 6/2005 | Takenaka et al. | 438/778 |
| 2005/0148101 A1* | 7/2005 | Bamdad et al. | 436/524 |
| 2006/0238766 A1* | 10/2006 | Polwart | 356/445 |
| 2007/0238162 A1* | 10/2007 | Miyamoto et al. | 435/287.2 |
| 2008/0124247 A1* | 5/2008 | Matsuoka et al. | 422/82.08 |

FOREIGN PATENT DOCUMENTS

| | | |
|---|---|---|
| JP | 2001-337083 | 12/2001 |
| JP | 2002-181703 | 6/2002 |
| JP | 2003-98091 | 4/2003 |

OTHER PUBLICATIONS

Microfilm of the specification and drawings annexed to the request of Japanese Utility Model Application No. 103245/1985 (Laid-open No. 10652/1987).

Microfilm of the specification and drawings annexed to the request of Japanese Utility Model Application No. 200124/1985 (Laid-open No. 108858/1987).

* cited by examiner (a)                (b)

(a)

(b)

(a)            (b)

FIBER SENSOR AND FIBER SENSOR DEVICE

CROSS REFERENCE TO RELATED APPLICATIONS

This is a U.S. national stage of application No. PCT/JP2005/021726, filed on 25 Nov. 2005. Priority under 35 U.S.C. §119(a) and 35 U.S.C. §365(b) is claimed from Japanese Application No. 2004-339774, filed 25 Nov. 2004, the disclosure of which is also incorporated herein by reference.

TECHNICAL FIELD

The present invention relates to an apparatus for measuring properties and reaction profiles of various types of materials by using a surface plasmon resonance (SPR) sensor, transmitted/reflected light intensity measurement, fluorescent light bar code recognition measurement, etc., and a method of manufacturing thereof, and more particularly to a fiber sensor and a fiber sensor apparatus, each using an optical fiber.

BACKGROUND ART

In quantum mechanics, among plasma waves of free electrons in metal, a plasma wave localized on the surface of metal is called surface plasmon. The surface plasmon is a mix of a plasma wave and an electromagnetic wave, and is transmitted along the surface of metal. In recent years, attention has been drawn to a technique of measuring materials located on the surface of metal by applying, by means of light, resonance-excitation (generation) to the surface plasmon. This measurement technique using the surface plasmon resonation (SPR) is noted in that interaction of biological material, such as protein, can be measured without chemically modifying pigment, etc., and that dynamic behaviors in the interaction can be grasped at high precision in real time.

A conventional plasmon sensor apparatus 10 using the above-mentioned measurement by SPR (hereinafter, referred to as "SPR apparatus") is shown in FIG. 19. The SPR apparatus 10 includes: a SPR sensor 1 formed at the fore end portion of a optical fiber 2; a light source 3 for emitting a light having a predetermined wavelength or frequency so as to output the light, via the beam splitter 4 and the fiber coupler 5a, to the SPR sensor 1; and a light detector 8 for detecting, via the beam splitter 4 and the fiber coupler 5a, a reflected light (light information) reflected at the SPR sensor 1. As the light source 3, a He—Ne laser light source or a halogen lamp is employed, whereas as the SPR sensor 1, a sensor of a frequency-variable type is employed because measurement is basically performed while keeping an incidence angle constant. Also, when using polarization, polarizing elements 5b, 5c, such as a ½ wavelength plate and a ¼ wavelength plate, are provided.

In the conventional SPR sensor apparatus 10 shown in FIG. 19, light emitted from the light source 3 is transmitted through the beam splitter 4 to be projected onto the measurement surface 6 of the SPR sensor 1 via the optical fiber 2. When the light is irradiated on the measurement surface 6, reflected light is generated at the measurement surface 6 and is introduced via the optical fiber 2 and the beam splitter 5 into the light detector 8. The reflected light supplied from the measurement surface 6 has a property that the intensity of the reflected light changes when a measurement object material 7, flowing in the direction shown by the arrow in the drawing (left to right facing the sheet), joins the measurement surface 6. Accordingly, by measuring the change in the intensity of the reflected light, a property and reaction of the measurement object material 7, and further the interaction between materials, etc. can be measured in real time.

Patent document 1: Japanese Patent application laid-open publication No. 2001-165852

DISCLOSURE OF INVENTION

Problem to be Solved by the Invention

However, in the above-mentioned conventional SPR apparatus, the shape of the measurement surface located at the fore end of the light introducing core of the SPR sensor is a cone having the diameter of 5 µm, which is so fine as to be easily broken. Further, there is a problem that a great deal of time is required to process it into the shape at high precision, thus processing being difficult.

Also, the measurement surface is formed by fixing a metal film onto both of a fore end of the cone-shaped light-introducing core and a fore end of the plane-shaped clad by evaporation, etc. There is another problem that, since the respective shapes of the fore ends are different from each other, their distances from the vapor deposition source are not the same, so that it is difficult to form (by vapor deposition) a uniform metal thin film.

Further, the SPR sensor is fixedly mounted on the specimen container through which the measurement object material is caused to flow so that the SPR sensor cannot be easily detached or mounted. Therefore, for example, when, after completing measurement of one measurement object material, another measurement object material is measured, the SPR sensor must be set again so that a great deal of time is required to prepare the measurement, which is further another problem.

Further, when properties of a plurality of measurement object materials are measured concurrently, a plurality of SPR sensors are required so that a great deal of time is needed to set the respective SPR sensors and also size of the SPR sensor apparatus itself becomes large, which is further another problem.

Further, in the SPR sensor apparatus, it is required to provide accessories, such as a SUS tube for supplying and discharging the measurement object material, and detection flow channel for allowing the measurement object material to be brought into contact with the SPR sensor, thereby causing further problems that the cost becomes high and that the size of the SPR sensor apparatus itself becomes large.

The present invention has been made in view of the above-mentioned circumstances, and it an object of the invention to provide a fiber sensor and a fiber sensor apparatus, each of which has a small size and a simple structure, and can perform high-precision and effective measurement, the fiber sensor and fiber sensor apparatus using a SPR sensor, transmitted/reflected light intensity measurement, and fluorescent bar code recognition measurement, etc.

Means for Solving Problem

In order to accomplish the above-mentioned object, the present invention provides the following configurations as means for solving the problems. Specifically, a first aspect of a fiber sensor according to the present invention provides a fiber sensor including: an optical waveguide unit having a measurement surface formed at an end of an optical waveguide; and a channel unit through which a specimen, serving as a measurement object to be measured by contact with the measurement surface, is caused to flow in and out via a specimen channel, wherein the optical waveguide is fixed to the optical waveguide unit such that the measurement surface forms a part of a channel wall surface of the channel unit, the optical waveguide unit is fixed to the channel unit, and the optical waveguide unit is arranged so as to be detachable from the channel unit.

A second aspect of a fiber sensor according to the present invention provides a fiber sensor including: an optical waveguide unit having a measurement surface formed at an end of an optical waveguide; and a channel unit through which a specimen, serving as a measurement object to be measured by contact with the measurement surface, is caused to flow in and out via a specimen channel, wherein the optical waveguide is arranged such that the measurement surface forms a part of a channel wall surface of the channel unit, and the optical waveguide comprises at least one optical waveguide.

A third aspect of a fiber sensor according to the present invention provides a fiber sensor, wherein the optical waveguide of the optical waveguide unit is arranged in an m×n structure at an arbitrary interval.

A fourth aspect of a fiber sensor according to the present invention provides a fiber sensor including: a first optical waveguide unit having a measurement surface formed at an end of an optical waveguide; a detecting unit for detecting light information supplied from the measurement surface; and a channel unit through which a specimen, serving as a measurement object to be measured by contact with the measurement surface, is caused to flow in and out via a specimen channel; wherein the optical waveguide is arranged in the first optical waveguide unit such that the measurement surface forms a part of a channel wall surface of the channel unit, and the optical information is provided by any of transmitted light, reflected light, fluorescent light and chemiluminescence from the measurement surface.

A fifth aspect of a fiber sensor according to the present invention provides a fiber sensor including: a first optical waveguide unit having a measurement surface formed at an end of an optical waveguide; a detecting unit for detecting light information supplied from the measurement surface; a second optical waveguide unit for transmitting light to the measurement surface; and a channel unit through which a specimen, serving as a measurement object to be measured by contact with the measurement surface, is caused to flow in and out via a specimen channel; wherein the optical waveguide is arranged in the first optical waveguide unit such that the measurement surface forms a part of a channel wall surface of the channel unit, and the optical information is provided by any of transmitted light, reflected light, and fluorescent light from the measurement surface.

A sixth aspect of a fiber sensor according to the present invention provides a fiber sensor including: an optical waveguide unit having a measurement surface formed at an end of an optical waveguide; and a channel unit through which a specimen, serving as a measurement object to be measured by contact with the measurement surface, is caused to flow in and out via a specimen channel; wherein the optical waveguide is arranged in the optical waveguide unit, a measurement surface forming connector is arranged on an end surface of the optical waveguide unit so as to cover at least a fore end portion of the optical waveguide, and a solvent containing metal particles is caused to flow in and out of the fore end portion of the optical waveguide via the measurement surface forming connector, thereby forming the measurement surface.

A seventh aspect of a fiber sensor according to the present invention provides a fiber sensor, wherein the optical waveguide unit and the channel unit are connected by means of a connector structure having a positioning pin so that the specimen channel is formed.

An eighth aspect of a fiber sensor according to the present invention provides a fiber sensor, wherein the optical waveguide unit has a flow-in and flow-out channel formed therein, through which a specimen, serving as a measurement object, or a detergent is caused to flow in and out of the channel unit.

An ninth aspect of a fiber sensor according to the present invention provides a fiber sensor, wherein the optical waveguide unit is provided with a capillary through which a specimen, serving as a measurement object, or a detergent is caused to flow in and out of the channel unit.

A tenth aspect of a fiber sensor according to the present invention provides a fiber sensor, wherein a solvent for forming a ligand layer is supplied to the measurement surface, and after the formation of a ligand layer, a specimen, serving as a measurement object, is supplied.

An eleventh aspect of a fiber sensor according to the present invention provides a fiber sensor, wherein the measurement surface is formed by means of a plasmon resonance (SPR) sensor.

A first aspect of a fiber sensor apparatus according to the present invention provides a fiber sensor apparatus including: the above-mentioned fiber sensor; at least one light source for supplying measuring light to be projected onto the measurement surface via the optical waveguide unit; and at least one light detecting unit for detecting light information supplied from the measurement surface.

A second aspect of a fiber sensor apparatus according to the present invention provides a fiber sensor apparatus, wherein the light detecting unit includes switching means for switching the light information from the measurement surface in terms of time or space.

A third aspect of a fiber sensor apparatus according to the present invention provides a fiber sensor apparatus, wherein the switching means includes a driving unit for rotating or moving one or more light shielding plates having one or more holes formed therein.

A fourth aspect of a fiber sensor apparatus according to the present invention provides a fiber sensor apparatus, wherein the switching means performs the switching by time-dividing an electric signal supplied from the detecting unit.

A fifth aspect of a fiber sensor apparatus according to the present invention provides a fiber sensor apparatus, wherein the switching means performs the switching by time-dividing a light signal supplied to the detecting unit.

A first aspect of a measuring method for use in a fiber sensor apparatus according to the present invention provides a measuring method for use in a fiber sensor apparatus, including the steps of: using a light detecting unit to detect chemiluminescence that is emitted from a measurement surface of a first optical waveguide unit via a specimen channel due to self-luminescence of the measurement surface; and measuring a property of a specimen, serving as a measurement object, based on the detected chemiluminescence.

A second aspect of a measuring method for use in a fiber sensor apparatus according to the present invention provides a measuring method for use in a fiber sensor apparatus, including the steps of: supplying light from a light source to an optical waveguide; projecting the light from the optical waveguide to a measurement surface formed at a position where the optical waveguide faces a specimen channel; using a light detecting unit to detect any of transmitted light, reflected light, and fluorescent light that is emitted from the light projected measurement surface; and measuring a property of the specimen, serving as measurement object, based on the detected light.

A third aspect of a measuring method for use in a fiber sensor apparatus according to the present invention provides a measuring method for use in a fiber sensor apparatus, including the steps of: supplying light from a single light source to a plurality of optical waveguides; concurrently projecting the light transmitted from the optical waveguides onto a plurality of measurement surfaces formed in a specimen channel; switching, in terms of time or space, light information in any of transmitted light reflected light, and fluorescent light that is emitted from the light projected measurement surfaces; and detecting the switched light information by means of a single light detecting unit.

A fourth aspect of a measuring method for use in a fiber sensor apparatus according to the present invention provides a measuring method for use in a fiber sensor apparatus, including the steps of: switching, in terms of time or space, light information of chemiluminescence that is emitted from a plurality of measurement surfaces formed in a specimen channel due to self-luminescence of the measurement surfaces; and detecting the switched light information by means of a single light detecting unit.

A fifth aspect of a measuring method for use in a fiber sensor apparatus according to the present invention provides a measuring method for use in a fiber sensor apparatus, wherein the switching uses a driving unit for rotating or moving one or more light shielding plates having one or more holes formed therein.

A sixth aspect of a measuring method for use in a fiber sensor apparatus according to the present invention provides a measuring method for use in a fiber sensor apparatus, wherein the switching is performed by time-dividing an electric signal supplied from the detecting unit.

A seventh aspect of a measuring method for use in a fiber sensor apparatus according to the present invention provides a measuring method for use in a fiber sensor apparatus, wherein the switching is performed by time-dividing, a light signal supplied to the detecting unit.

ADVANTAGES OF THE INVENTION

In a fiber sensor of the present invention, an optical waveguide is arranged such that a measurement surface thereof forms a part of a channel wall surface of a channel unit, and the optical waveguide is detachable from an optical waveguide unit. Accordingly, the measurement surface and the channel unit each can easily be replaced when either of them is deteriorated or broken.

Further according to a fiber sensor of the present invention, the optical waveguide is arranged such that the measurement surface forms a part of a channel wall surface of the channel unit. The optical waveguide is composed of at least one or more optical waveguides. Hence, the measurement surface can be integrated in a multi-fiber measurement structure, so that the property of many specimens can be measured at one time.

Further, according to the present invention, an fiber sensor includes a first optical waveguide unit having a measurement surface formed at an end of an optical waveguide, a detecting unit for detecting light information supplied from the measurement surface, a second optical waveguide unit for transmitting light to the measurement surface, and a channel unit through which a specimen, serving as a measurement object to be measured by contact with the measurement surface, is caused to flow in and out via a specimen channel. The optical waveguide is arranged in the first optical waveguide unit such that the measurement surface forms a part of a channel wall surface of the channel unit. The optical information is provided by any of transmitted light, reflected light, and fluorescent light from the measurement surface. Accordingly, signal to noise (SN) ratio is improved compared with the conventional reflected light system, thereby enabling high precision measurement.

Further, in a fiber sensor according to the present invention, an optical waveguide is arranged in an optical waveguide unit such that a measurement surface thereof serves as a part of a channel wall surface of the channel unit. A solvent containing metal particles is caused to flow in and out of the measurement surface via flow-in and flow-out channels formed in a channel unit so as to form a thin film for the measurement surface. Accordingly metal particles can easily be supplied to form the measurement surface. The metal particles can easily be deposited at a position where the measurement surface of the optical waveguide is to be formed. In addition, a flow rate or flow direction of the solvent containing metal particles is controlled in order that the thickness of the thin film made of metal particles, or the shape of the sensor can be controlled, and a thin film having uniform thickness can be formed.

Further, in a fiber sensor according to the present invention, a detergent can easily be supplied to the channel unit so that the channel unit can simply be washed without being detached from the optical waveguide unit.

Further, In a fiber sensor of the present invention, using two or more optical waveguides, each having a measurement surface at the end thereof, a various solvent can be supplied to respective measurement surfaces to form different types of ligand layers, and a specimen serving as measurement object is supplied after the formation of the ligand layers, whereby various types of measurements can be performed effectively.

According to the present invention, there is provided a fiber sensor apparatus which comprises the above-mentioned fiber sensor, at least one light source for supplying measuring light to be projected onto the measurement surface via an optical waveguide unit, at least one light detecting unit for detecting light information supplied from the measurement surface, and a switching unit. Hence, the size of the overall apparatus can be made small.

According to a method of measuring the specimen of the present invention, light from a light source is supplied to an optical waveguide. The light from the optical waveguide is projected onto a plurality of measurement surfaces formed in a specimen channel. A light detecting unit is used to detect transmitted light reflected light, fluorescent light, or chemiluminescence that is emitted from the light projected measurement surfaces. A property of a specimen, serving as measurement object, is measured based on the detected light of transmitted light, reflected light, fluorescent light, or chemiluminescence, whereby the specimen can be measured at higher precision.

Further, a method of measuring a specimen according to the present invention, comprising: supplying light from a single light source to a plurality of optical waveguides; concurrently projecting the light transmitted from the optical waveguides onto a plurality of measurement surfaces formed in a specimen channel; and detecting respective light information of transmitted light, reflected light, fluorescent light, chemiluminescence, or the like that is emitted from the light projected measurement surfaces and switching the light information in terms of time or space by means of a single light detecting unit. Thus, many specimens can be measured at one time at higher precision.

Figure 1:
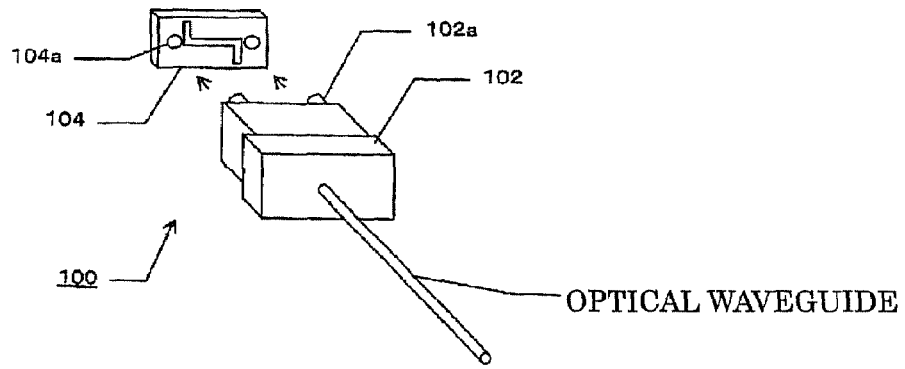
FIG. 1 is a schematic view showing a configuration of an embodiment of a fiber sensor according to the present invention.

EXPLANATIONS OF LETTERS AND NUMERALS 100, 120, 140, 172 fiber sensor
102 optical waveguide unit
102a engagement protruding portion
103a flow-in channel
103b flow-out channel
104 channel unit
104a engagement hole
105a flow-in tube
105b flow-out tube
106 optical waveguide
106a fore end portion
107 measurement surface forming connector
108 measurement surface
109 glass tube
110 specimen supplying port
112 specimen channel
114 specimen discharging port
122 optical waveguide unit
124 flow-in channel
126 flow-out channel
128 channel
150 ligand forming jig
152 ligand solvent supplying tube
154 ligand supplying connector
156 acceptor unit
156a, 156b through hole
158 ligand solvent discharging tube
160 ligand discharging connector
162 acceptor bead
170 fiber sensor apparatus
174 light source
176 measuring unit

MODES FOR CARRYING OUT THE INVENTION

Hereinafter, embodiments of the present invention will described with reference to the attached drawings.

FIG. 1 is a perspective view showing an embodiment of a fiber sensor 100 according to the present invention. The fiber sensor 100 is so constituted that a channel unit 104 is attached to an optical waveguide unit 102 by means of a connector structure. The term "connector structure" refers to a structure in which an engagement protruding portion 102a adapted to be engaged with an engagement hole 104a formed in the channel unit 104 is formed in the optical waveguide unit 102, and the engagement hole 104a and the engagement protruding portion 102a are joined, thereby enabling connection therebetween while insuring easy positioning. An alternative configuration, while not shown in the drawing, may be adopted in which an engagement hole is formed in the optical waveguide unit 102 instead of forming the engagement protruding portion 102a, and the optical waveguide unit 102 is connected to the channel unit 104 by means of an insertion pin, or the like. Alternatively, as necessary, a fixing clip for fixedly connecting the both units may be used.

Figure 2:
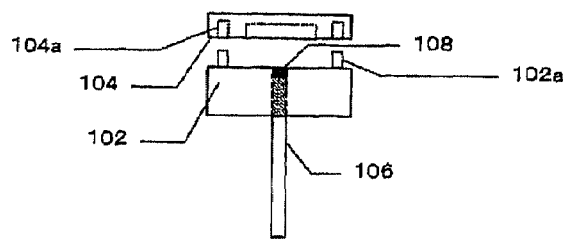
FIG. 2 is a top view showing the fiber sensor of the present invention shown in FIG. 1.

Next, descriptions will be made as to the optical waveguide unit 102. As shown in FIG. 2, the optical waveguide unit 102 is formed at the fore end portion 106a by plasmon resonance (SPR), or by setting and fixing an optical waveguide 106 having a measurement surface 108 to which a reflecting multilayer film or mirror surface treatment is applied. It should be noted that the optical waveguide 106 is so fixed to the optical waveguide unit 102 that the measurement surface 108 serves as a part of a channel wall surface of the channel unit 104.

Although in FIG. 2 the optical waveguide 106 is so fixed that the measurement surface 108 is positioned on the same surface as the end surface of the optical waveguide unit 102, the optical waveguide 106 may be fixed on a surface different from the end surface of the optical waveguide unit 102 so long as the optical waveguide 106 is formed as part of the wall surface of the channel unit 104.

Figure 3:
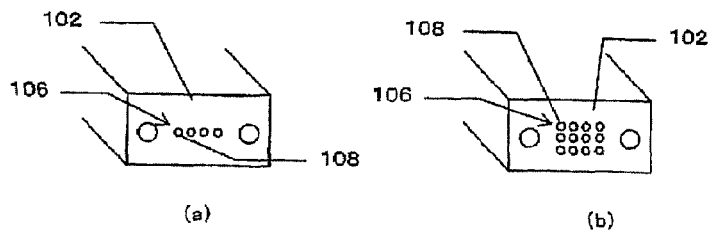
FIG. 3(a) and FIG. 3(b) are schematic views each showing a configuration of an embodiment of an optical waveguide unit in a fiber sensor according to the present invention.

Further, in the optical waveguide unit 102, as shown in FIG. 3(a) and FIG. 3(b), the optical waveguide 106 may be constituted in a multi-fiber arrangement. The optical waveguide 106 are constituted in an m×n arrangement, wherein examples of a one-dimensional arrangement include a 1×4 arrangement as shown in FIG. 3(a), and examples of a two-dimensional arrangement include a 3×4 arrangement as shown in FIG. 3(b), thus the arrangement thereof not being limited to a specific one. The fore end of each optical waveguide 106 is provided with a measurement surface 108, so that as many measurements of specimens as the provided optical waveguides 106 can be performed at one time.

Figure 4:
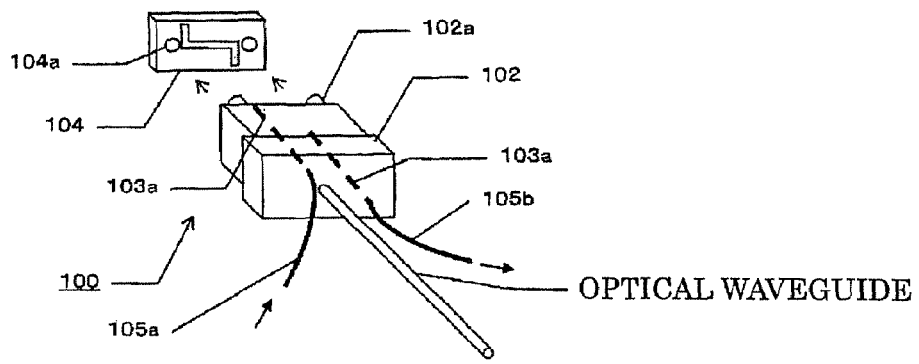
FIG. 4 is a schematic view showing a configuration of an embodiment of a fiber sensor according to the present invention.
Figure 7:
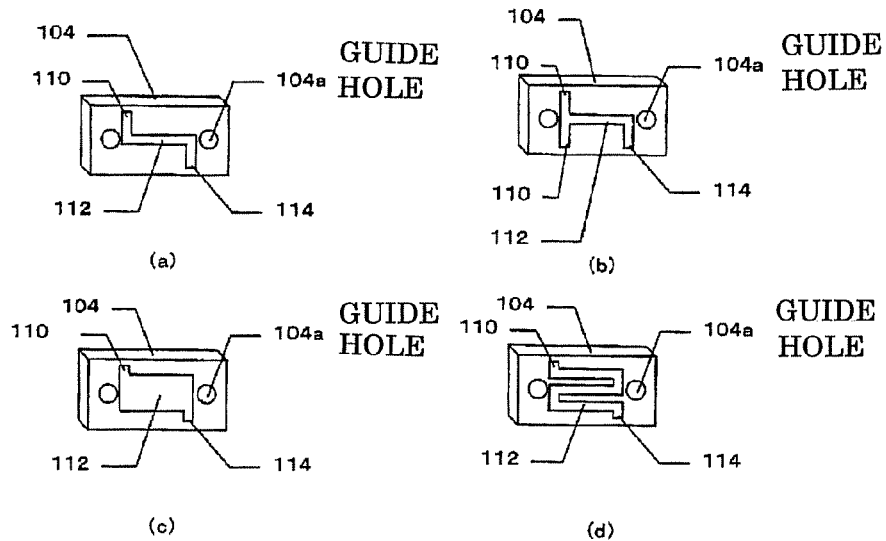
FIG. 7(a) to FIG. 7(d) are schematic views each showing a configuration of an embodiment of a fiber sensor according to the present invention.

Further, as shown in FIG. 4, in the optical waveguide unit 102, a flow-in channel 103a and a flow-out channel 103b for allowing a specimen to flow in and out may be formed as required. In this configuration, one end of the flow-in channel 103a is connected to the flow-in tube 105a, and the other end of the flow-in channel 103a is connected to the specimen supplying port 110 (see FIG. 7) of the channel unit 104 as later described. Also, one end of the flow-out channel 103b is connected to the flow-out tube 105b, and the other end of the flow-out channel 103b is connected to a specimen discharging port 114 (see FIG. 7) of the channel unit 104 as later described.

Figure 5:
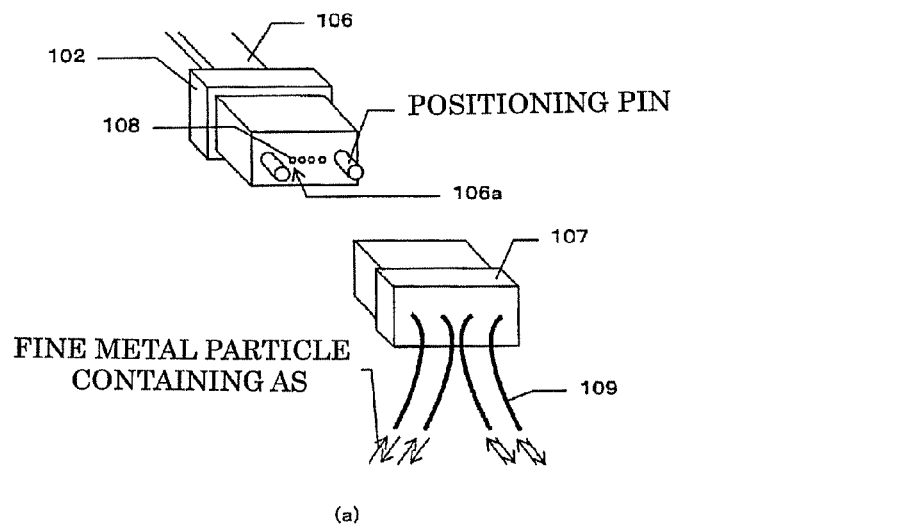
FIG. 5(a) and FIG. 5(b) are schematic views each illustrating an embodiment of a fiber sensor according to the present invention.
Figure 5:
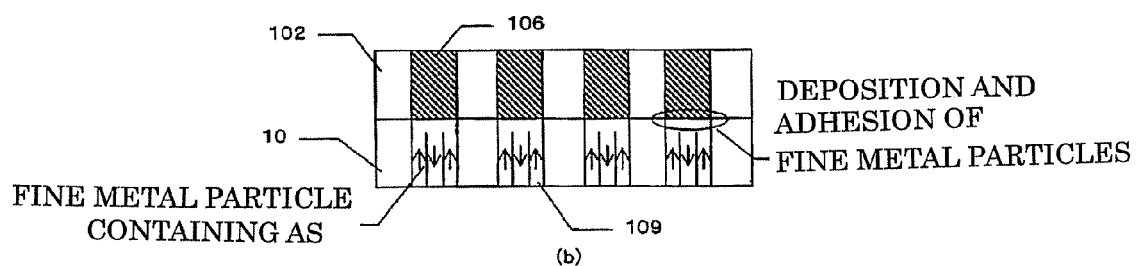
Figure 6:
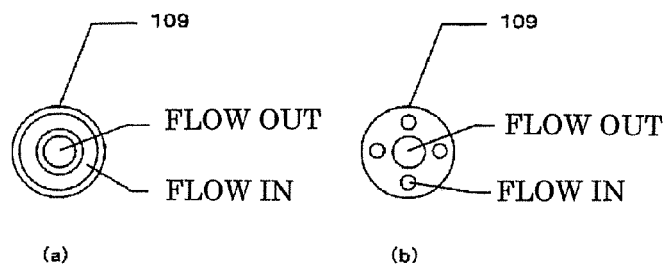
FIG. 6(a) and FIG. 6(b) are schematic views each showing a cross section of an embodiment of a fiber sensor according to the present invention.

Next, a method of forming the measurement surface 108 will be described with reference to FIG. 5(a) and FIG. 5(b). FIG. 5(a) is a perspective view showing a configuration in which the measurement surface 108 has not been formed yet, whereas FIG. 5(b) is a partially enlarged sectional view showing a configuration in which the measurement surface 108 has been already formed (after assembly is completed). Firstly, an optical waveguide 106 is attached to the optical waveguide unit 102, and the measurement surface is disposed oppositely to a measurement surface forming connector 107 to which a glass tube 109 (see FIG. 6 for detailed arrangement) for allowing a solvent containing metal particles to flow in and out of the optical waveguide unit 102 is provided. A solvent containing metal particles is supplied via the glass tube 109 and the measurement surface forming connector 107 to the fore end portion 106a of the optical waveguide 106, thereby forming the measurement surface 108. The film thickness of the measurement surface 108 can be controlled by changing a supply amount, a supply rate, etc. of the solvent. It should be noted that the channel unit 104 shown in FIG. 1 may be substituted for the measurement surface forming connector 107.

In FIG. 5(a) and FIG. 5(b), descriptions are made as to the optical waveguide 106 having a multi-fiber structure. By providing the glass tube 109 to the measurement surface forming connector 107 in the form of a multi-fiber structure, measurement surfaces 108 can be formed on the fore ends of a plurality of optical waveguides 106 at one time. It should be noted that the multi-fiber structure of the optical waveguide 106 is applicable to the single-fiber structure.

In the above-mentioned configuration, ligand can be formed on the measurement surface. By supplying a plurality of types of ligand solvents to each measurement surface of the optical waveguide having the multi-fiber structure, a plurality of types of ligand can be formed. Since this technique can be performed in the state in which the connector structure is incorporated, a plurality of types of measurements of specimens can be performed in an effective manner.

Next, with reference to FIG. 6(a) and FIG. 6(b), an example of the glass tube 109 connected to the measurement surface forming connector 107 shown in FIG. 5(a) and FIG. 5(b) will be described. The glass tube 109 shown in FIG. 6(a) has a double-tube arrangement having a circular cross section and two-layer structure, wherein the tube on the inner layer side is used for discharging a solvent, and the tube on the outer layer side is used for supplying a solvent. The glass tube 109 shown in FIG. 6(b) has a multi-tube arrangement having a circular cross section and two-layer structure, wherein the tube on the inner layer side is used for discharging a solvent, and the four tubes on the outer layer side are used for supplying a solvent. It should be noted that the structure of the glass tube 109 is not limited to those shown in FIG. 6(a) and FIG. 6(b). For example, the supplying tube and the discharging tube may be used for their reverse purposes. Also, the number of the supplying tubes shown in FIG. 6(b) is not limited to four, so that the number can be changed as necessary.

As shown in FIG. 6(a) and FIG. 6(b), when the inner and outer tubes of the two-layer-structured glass tube 109 are used appropriately between solvent discharging and supplying purposes depending on the situation, the thickness of formed metal film can be controlled, thereby enabling adjustment of sensor sensitivity.

Next, the channel unit 104 will be described. As shown in FIG. 7(a) to FIG. 7(d), the channel unit 104 is provided with a specimen supplying port 110 for supplying a specimen serving as a measurement object, a specimen channel 112 for allowing a specimen to flow, and a specimen discharging port 114 for discharging the specimen. Examples of the channel shape of the specimen channel 112 include, as shown in FIG. 7(a) to FIG. 7(d), (a) a basic type, (b) a reacted-material detecting type, and (c), (d) two-dimensional array adaptive types, thus the type of shape being selectable in view of the purpose of measurement and not limited to a specific one. Also, any shape can be adopted so long as the shape insures that the measurement surface 108 (see FIG. 2) formed at the fore end of the optical waveguide 106 serves as a part of the wall surface of the specimen channel 112.

Figure 8:
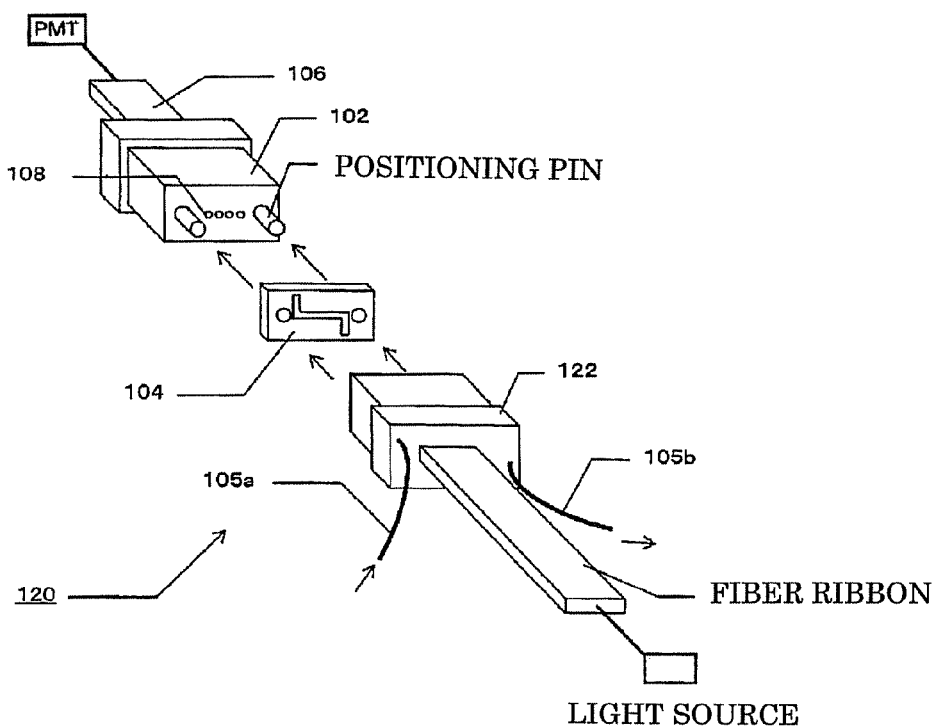
FIG. 8 is a schematic view showing an embodiment of a configuration of a fiber sensor according to the present invention.

Next, with reference to FIG. 8, another embodiment of the fiber sensor 120 will be described. It should be noted that descriptions will be made while denoting the same letter or numeral with respect to the same constituent elements as those in the fiber sensor 100 shown in FIG. 1. The fiber sensor 120 shown in FIG. 8 is constituted by adding a second optical waveguide unit 122 to the fiber sensor 100 shown in FIG. 1. The second optical waveguide unit 122 is so provided as to be opposed to the first optical waveguide channel unit 102 with the channel unit 104 interposed therebetween, and to supply light to the measurement surface 108 that is formed in the optical waveguide 106 attached to the first optical waveguide unit 102. Accordingly, the fiber sensor 120 shown in FIG. 8 is so configured that light for measurement, input from the light source provided at the second optical waveguide unit 122 side, is projected onto the measurement surface 108, and that transmitted light, fluorescent light, or chemiluminescence supplied from the measurement surface 108 is received via the first optical waveguide unit 102 by a detecting unit.

Figure 14:
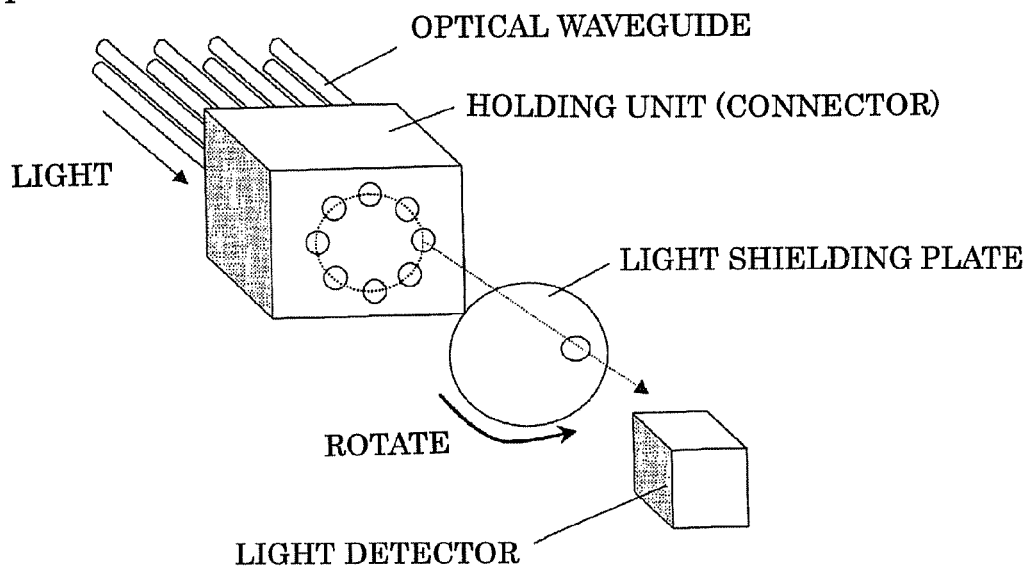
FIG. 14 is a view showing a manner that, when a plurality of optical waveguides are arranged in the form of a circle, and one detector is provided, switching in terms of space is performed by rotatably moving a light shielding or interrupting plate.

In the detecting unit, when a plurality of optical waveguides is provided, it is sufficient to provide one or more light detectors. For a single light detector, it is sufficient that switching in terms of space (space de-multiplexing) is performed by moving, for example, rotating the light shielding or interrupting plate as shown in FIG. 14, or alternatively the signal supplied from the detector may be switched in terms of time while keeping the movement of the light shielding plate constant.

Figure 15:
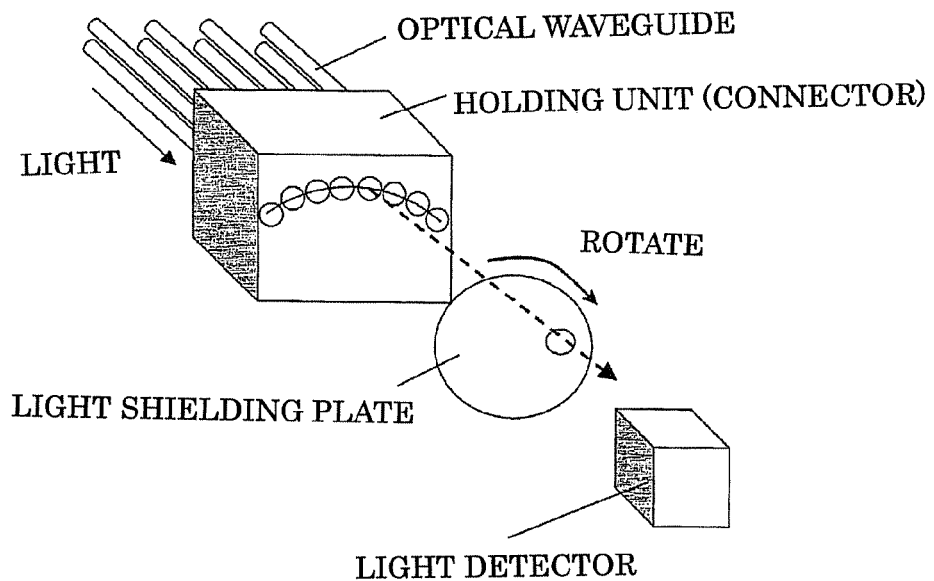
FIG. 15 is a view showing a manner that, when a plurality of optical waveguides are arranged in the form of an arc, and one detector is provided, switching in terms of space is performed by rotatably moving a light shielding plate.
Figure 16:
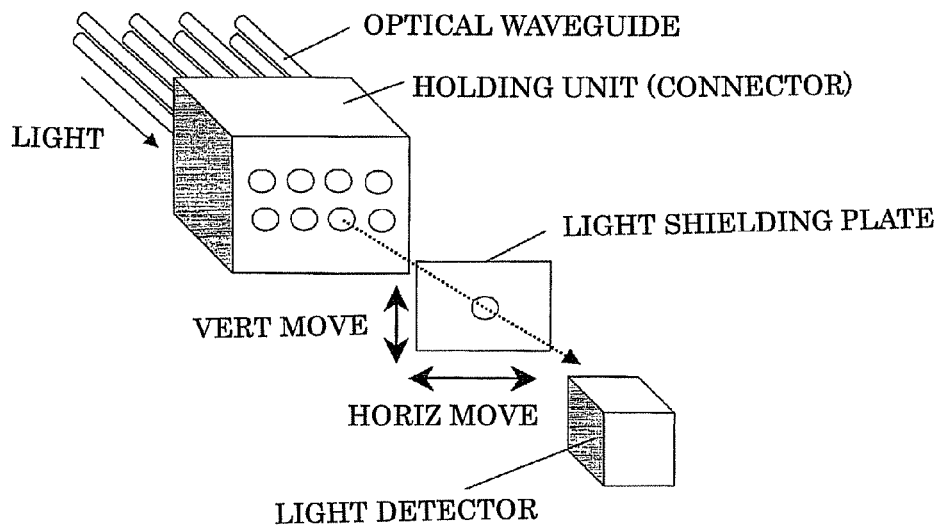
FIG. 16 is a view showing a manner that, when a plurality of optical waveguides are arranged in the form of a line and two-dimensionally, and one detector is provided, switching in terms of space is performed by vertically moving or linearly moving a light shielding plate.
Figure 17:
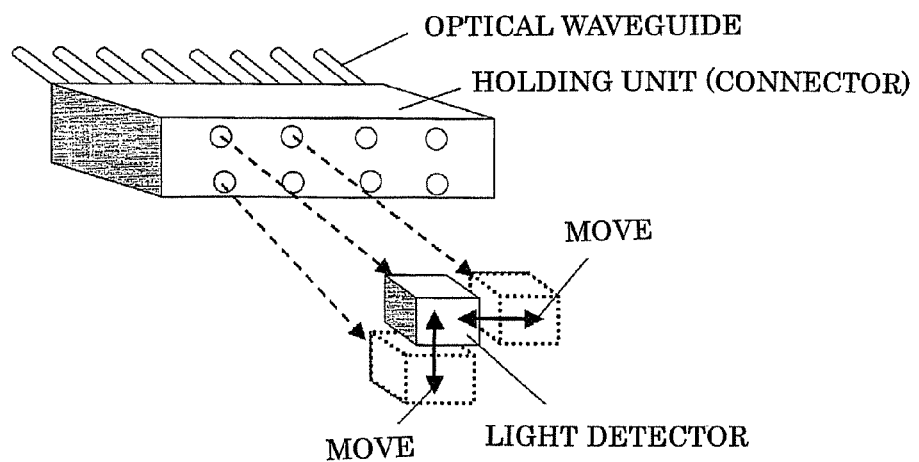
FIG. 17 is a view showing a manner that, when a plurality of optical waveguides are arranged two-dimensionally, and one detector is provided, switching in terms of space is performed by moving the detector.
Figure 18:
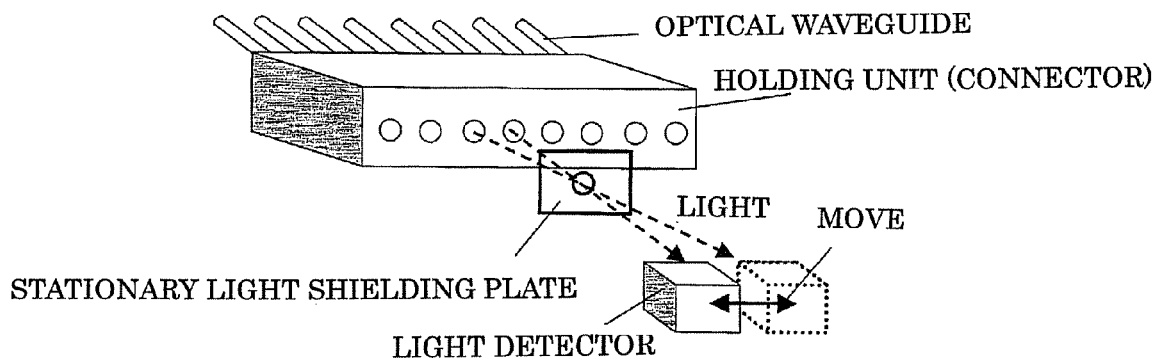
FIG. 18 is a view showing a manner that, when a plurality of optical waveguides are arranged linearly, one detector is provided, and a light shielding plate is fixedly provided, switching in terms of space is performed by moving the detector.
Figure 19:
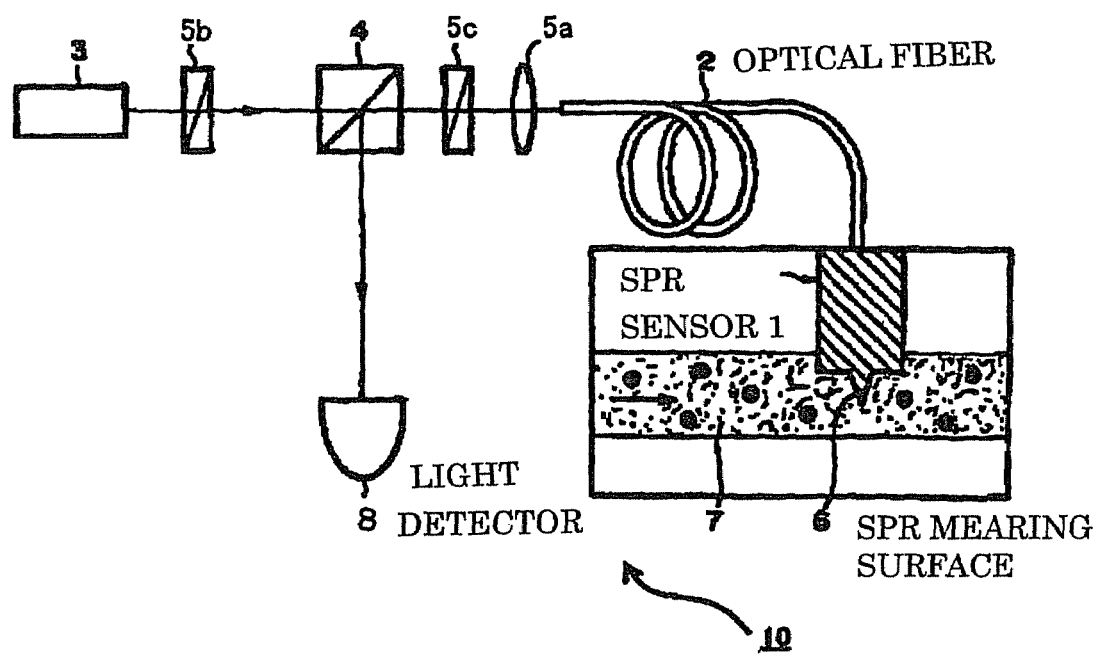
FIG. 19 is a schematic view showing a configuration of a conventional plasmon sensor apparatus.

With respect to the manner of moving the light shielding plate, as shown in FIG. 15 and FIG. 16, any form or locus coping with the shape of the optical waveguides, including a straight line, an arc, a two-dimensional arrangement and a three-dimensional arrangement, is allowable so long as switching can be performed. With respect to the shape of the light shielding plate, any shape, including a circle and a square, is allowable so long as the selected signal can be transmitted. Alternatively, the detector may be moved as shown in FIG. 17. With respect to the manner of moving the light detector, any form or locus coping with the shape of the optical waveguides, including a straight line, an arc, two-dimensional arrangement, and three-dimensional arrangement, is allowable so long as switching can be performed. Also, as shown in FIG. 18, the light detector may be moved while being combined with a fixedly provided light shielding plate. Alternatively, instead of moving the light detector, a plurality of light detectors may be provided.

Note that a configuration, while not shown in the drawing, can be adopted in which instead of providing the light source on the second optical waveguide side (see FIG. 1), both of the light source and the detecting unit are provided on the first light waveguide side. In this configuration, light for measurement is introduced from the first optical waveguide, and the optical path thereof is so shifted by means of a prism, a mirror or the like that the reflected light supplied from the measurement surface 108 is transmitted via the first optical waveguide, and supplied, at an optional point in the course of the optical path, to the detecting unit. This configuration is applicable to both of the cases where the number of the provided optical waveguides is single and plural.

Figure 9:
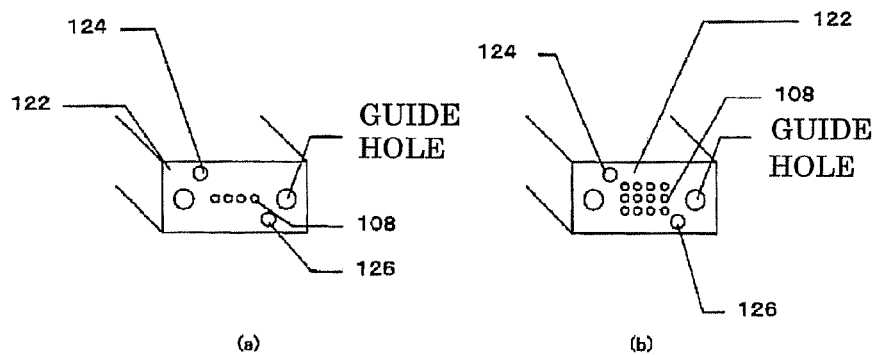
FIG. 9(a) and FIG. 9(b) are schematic views each showing a configuration of an embodiment of a fiber sensor according to the present invention.

Note that the second optical waveguide unit 122 has a multi-fiber structure in which as many optical waveguides for light irradiation as the optical waveguides provided at side for receiving measuring light as shown in FIG. 9. This is because multi-fiber (many types of) measurements can be performed concurrently. It should be noted that, while not shown in the drawing, the number of the optical waveguides to be provided at the second optical waveguide unit 122 is not necessarily the same as the number of the optical waveguides to be provided at the first optical waveguide unit 102. It is sufficient to provide optical waveguides of the number equal to or larger than the minimum number enabling reception of light information supplied from the measurement surface 108.

Also, in the second optical waveguide unit 122, as shown in FIG. 9, a configuration may be adopted in which a flow-in channel 124 and a flow-out channel 126 for allowing a specimen to flow in and out are provided as required. In this configuration, one end of the flow-in channel 124 is connected to a flow-in tube 105a, and the other end of the flow-in channel 124 is connected to the specimen supplying port 110 (see FIG. 7) of the channel unit 104. Also, one end of the flow-out channel 126 is connected to a flow-out tube 105b, and the other end of the flow-out channel 126 is connected to the specimen discharging port 114 (see FIG. 7) of the channel unit 104.

Figure 10:
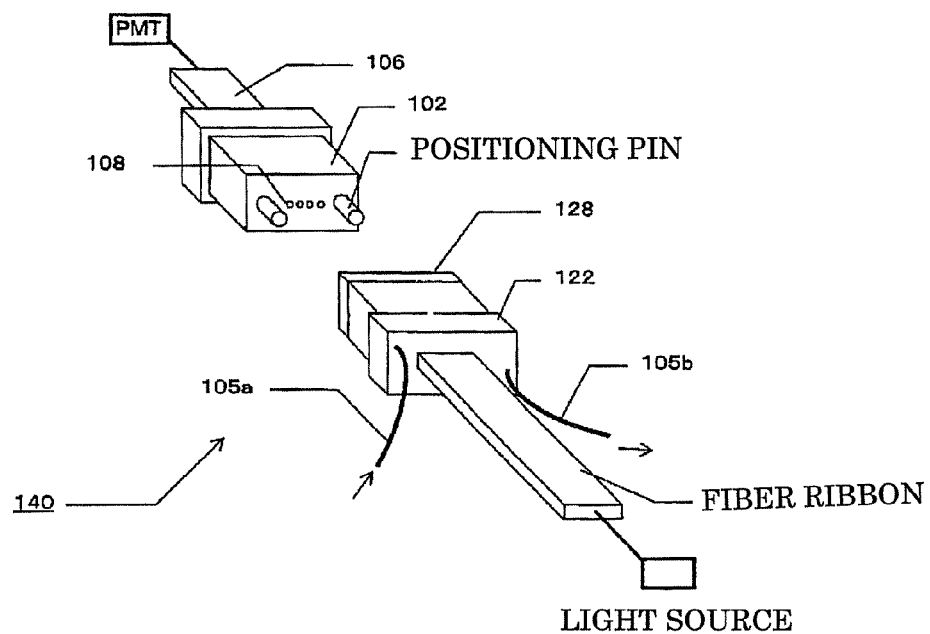
FIG. 10 is a schematic view showing an embodiment of a configuration of a fiber sensor according to the present invention.

Next, another embodiment of FIG. 8 and FIG. 9 will be described with reference to FIG. 10. In the fiber sensor 140 shown in FIG. 10, instead of providing the channel unit, a channel 128 for allowing a specimen to flow is provided on the end surface of the second optical waveguide unit. Other than this feature, the configuration of this embodiment is the same as that of FIG. 8. This configuration makes provision of the channel unit unnecessary, thus the configuration being more simplified.

Figure 11:
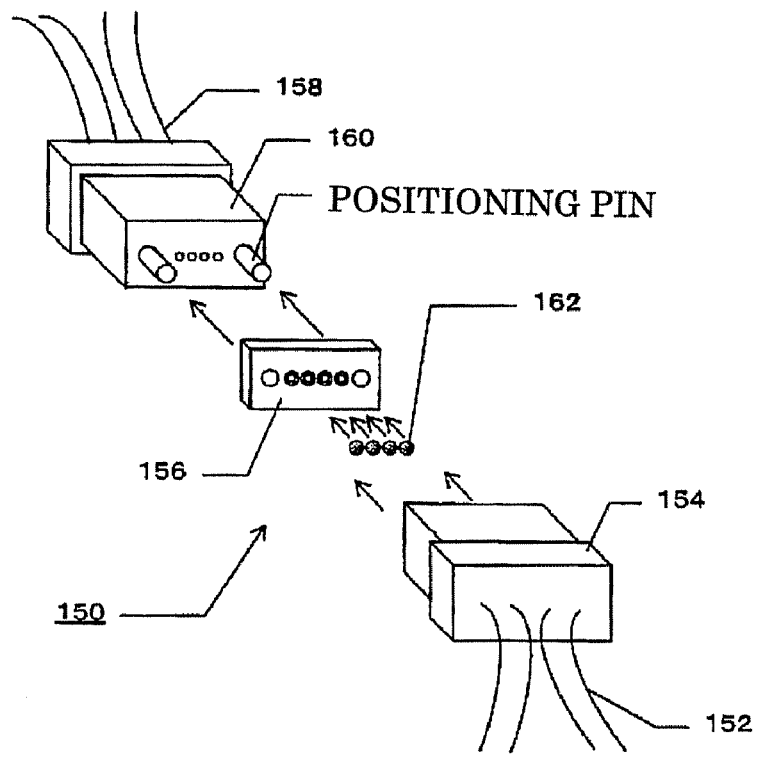
FIG. 11 is a schematic view showing a ligand forming method as an embodiment of the fiber sensor according to the present invention.
Figure 12:
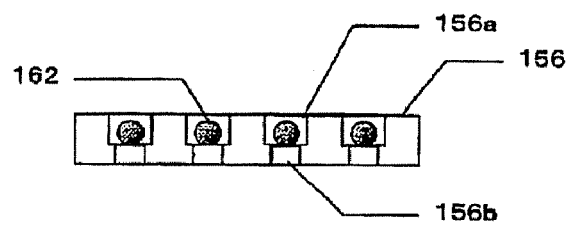
FIG. 12 is a partially enlarged view showing the ligand forming method shown in FIG. 11.

Next, with reference to FIG. 11, another embodiment of the ligand forming method will be described. In the ligand forming jig 150 shown in FIG. 11, a ligand supplying connector 154 having a ligand solvent supplying tube 152, an acceptor unit 156, and a ligand discharging connector 160 having ligand solvent discharging tube 158 are sequentially connected by means of a connector structure. It should be noted that, in the acceptor unit 156, as shown in FIG. 12, two through holes 156a and 156b having the respectively different diameters are formed at a plurality of locations, wherein in the respective through holes having larger diameters (in FIG. 12, the through hole 156a), an acceptor bead 162 serving as measurement object specimen is accommodated. Also, as the ligand solvent supplying tube 152 and the ligand solvent discharging tube 158, the tubes having the above-mentioned structure shown in FIG. 6(a) and FIG. 6(b) may be used.

Next, with reference to FIG. 11 and FIG. 12, a method of accommodating the acceptor bead 162 in the acceptor unit 156 by using the ligand forming jig 150 will be described. First, the ligand supplying connector 154, the acceptor unit 156, and the ligand discharging connector 160 are connected by means of the connector structure. At this occasion, the acceptor unit 156 is so connected that the through hole 156a, having a larger diameter, is directed toward the ligand supplying connector 154 side.

Next, a ligand solvent containing the acceptor beads 162 is supplied via the ligand solvent tube 152 and ligand supplying connector 154 to the acceptor unit 156. The acceptor unit 156 is so designed that the acceptor beads 162 do not pass through the through hole 156b, having a smaller diameter, whereby the acceptor beads 162 are trapped (accommodated) in the acceptor unit 156. Incidentally, unnecessary solvent is caused to pass through the acceptor unit 156, and to be discharged via the ligand discharging connector 160 from the ligand solvent discharging tube 158.

As described above, the specimen (acceptor beads 162) formed in the acceptor unit 156 is measured with the configuration in which it is incorporated as a substitute of the channel unit in the fiber sensor as shown in FIG. 1 or FIG. 8. In this configuration, at the fore end of the optical waveguide provided in the optical waveguide unit, the measurement surface does not need to be provided. In the configuration shown in FIG. 1, while not shown in the drawing, measurement of the specimen is so performed that light is irradiated from the optical waveguide unit onto the specimen and light reflected from the specimen is measured. In the configuration shown in FIG. 8, as shown in FIG. 14, measurement of the specimen is so performed that light is irradiated from the first optical waveguide unit onto the specimen and the light transmitted from the specimen is detected via the optical waveguide by the detecting unit. Also, when fluorescent light bar code recognition is completed with respect to the acceptor beads, measurement of the specimen is performed by measuring the fluorescent light supplied from the acceptor beads.

Next, with reference to FIG. 13, an embodiment of a fiber sensor apparatus will be described. The fiber sensor apparatus 170 shown in FIG. 13 further includes, in addition to the fiber sensor 172 shown in FIG. 8, a light source 174 for generating measuring light, and a measuring unit 176 for receiving and analyzing light information supplied from the measurement surface, such as transmitted or reflected light, fluorescent light, and chemiluminescence. In the fiber sensor apparatus 170, a plurality of optical waveguides including the measurement surface of the fiber sensor 172 are provided (see FIG. 8 for the details), whereas only a single light source 174 and only one measuring unit 176 are provided. Accordingly, measuring light is, after the measuring light is output from the a single light source 174, is divided by a splitter or the like, and transmitted to the plurality of light waveguides provided at the irradiation side. Also, measurement is so performed that transmitted light, fluorescent light, chemiluminescence, etc. supplied from a plurality of measurement surfaces are received by the optical waveguides provided at the light receiving side, and switching in terms of time or space is performed at the measuring unit 176.

When a plurality of optical waveguides are provided, it is sufficient to provide one or more light detectors. When one light detector is provided, it is sufficient that switching in terms of space is performed by moving, for example, rotating the light shielding plate, or alternatively the signal supplied from the detector may be switched in terms of time while keeping the movement of the light shielding plate constant. With respect to the manner of moving the light shielding plate, as shown in FIG. 15 and FIG. 16, any form or locus coping with the shape of the optical waveguides, including a straight line, an arc, a two-dimensional arrangement, and a three-dimensional arrangement, is allowable so long as switching can be performed. With respect to the shape of the light shielding plate, any shape, including circle and rectangle, is allowable so long as the selected signal can be transmitted. Alternatively, the detector may be moved as shown in FIG. 17. With respect to the manner of moving the light detector, any form or locus coping with the shape of the optical waveguides, including straight line, arc, two-dimensional arrangement and three-dimensional arrangement, is allowable so long as switching can be performed. Also, as shown in FIG. 18, the light detector may be moved while being combined with a fixedly provided light shielding plate. Alternatively, instead of moving the light detector, a plurality of light detectors may be provided. Accordingly, in the fiber sensor apparatus, while not shown in the drawing, as many measurements of specimens as the optical waveguides 106 can be performed.

Next, with reference to FIG. 13, a method of measuring a specimen using a fiber sensor apparatus 170 will be described. First, measuring light is supplied from the light source 172 to a plurality of optical waveguides. At this occasion, while not shown in the drawing, measuring light supplied from the light source 172 is split by means of 1×n (n denotes the number of the optical waveguides provided at the light irradiating side) splitters. Thereafter, the measuring light, transmitted via the optical waveguide provided at the irradiation side, is irradiated onto the measurement surface formed at the fore end portion of the optical waveguide. In the measurement surface, a ligand layer is formed, and a specimen is so held as to be trapped in the ligand layer. According to the state of the specimen, the state of transmitted light supplied from the measurement surface changes. Next, the transmitted light emitted from the measurement surface is received by the optical waveguide provided at the light receiving side, and finally the property of the specimen serving as measurement object is measured on the basis of the light information, such as transmitted light, reflected light, fluorescent light, or chemilumination, detected at the measuring unit 176. It should be noted that, when a plurality of optical waveguides are provided at the light irradiating side and at the light receiving side, detection is performed by switching, in terms of time or space by means of one detecting unit, light information, such as transmitted light, reflected light, fluorescent light, or chemiluminescence, emitted from the respective measurement surfaces.

When a plurality of optical waveguides are provided, it is sufficient that switching in terms of space is performed by moving, for example, rotating the light shielding plate as shown in FIG. 14, or alternatively the signal supplied from the detector may be switched in terms of time while keeping the movement of the light shielding plate constant. With respect to the manner of moving the light shielding plate, as shown in FIG. 15 and FIG. 16, any form or locus coping with the shape of the optical waveguides, including a straight line, an arc, a two-dimensional arrangement and a three-dimensional arrangement, is allowable so long as switching can be performed. With respect to the shape of the light shielding plate, any shape, including a circle and a rectangle, is allowable so long as the selected signal can be transmitted. Alternatively, the light detector may be moved as shown in FIG. 17. With respect to the manner of moving the light detector, any form or locus coping with the shape of the optical waveguides, including a straight line, an arc, a two-dimensional arrangement and a three-dimensional arrangement, is allowable so long as switching can be performed. Also, as shown in FIG. 18, the light detector may be moved while being combined with a fixedly provided light shielding plate.

Figure 13:
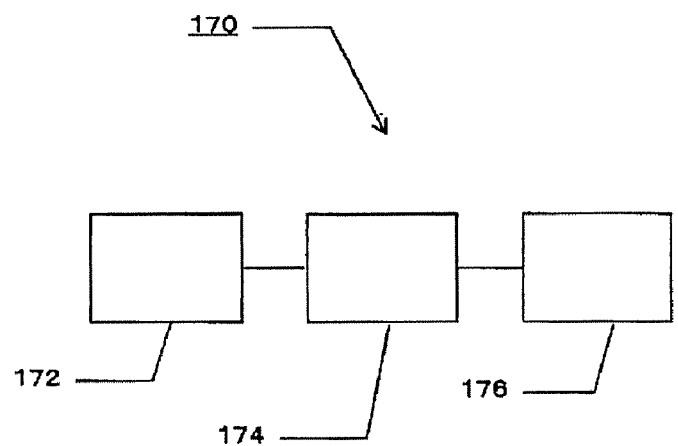
FIG. 13 is a schematic view showing a configuration of an embodiment of a fiber sensor apparatus according to the present invention.

It should be noted that, while not shown in the drawing, the optical waveguide unit used in the above-mentioned fiber sensors 100, 120, 140 and 172 and in the fiber sensor apparatus 170 shown in FIG. 13 may be so configured that the end surface is tilt. Preferably, the tilt angle of the end surface is set to 8 degree with respect to the direction in which light is transmitted (optical axis). With this configuration, even when a return light is generated by some cause, it does not return to the light source, so that control of light can be performed in a preferable manner.

The invention claimed is:

1. A fiber sensor comprising:
    an optical waveguide unit having a measurement surface formed at an end of an optical waveguide; and
    a channel unit through which a specimen, serving as a measurement object to be measured by contact with the measurement surface, is caused to flow in and out via a specimen channel; wherein
    the optical waveguide is fixed to the optical waveguide unit such that the measurement surface forms a part of a channel wall surface of the channel unit; and
    the optical waveguide unit is arranged so as to be detachable from the channel unit.

2. A fiber sensor comprising:
    an optical waveguide unit having a measurement surface formed at an end of an optical waveguide; and
    a channel unit through which a specimen, serving as a measurement object to be measured by contact with the measurement surface, is caused to flow in and out via a specimen channel;
    wherein the optical waveguide is arranged such that the measurement surface forms a part of a channel wall surface of the channel unit; and
    the optical waveguide comprises at least one optical waveguide.

3. The fiber sensor according to claim 2, wherein the optical waveguide of the optical waveguide unit is arranged in an m×n structure at an arbitrary interval.

4. A fiber sensor comprising:
    a first optical waveguide unit having a measurement surface formed at an end of an optical waveguide;
    a detecting unit for detecting light information supplied from the measurement surface; and a channel unit through which a specimen, serving as a measurement object to be measured by contact with the measurement surface, is caused to flow in and out via a specimen channel, wherein the optical waveguide is arranged in the first optical waveguide unit such that the measurement surface forms a part of a channel wall surface of the channel unit, and the light information is provided by any of transmitted light, reflected light, fluorescent light and chemiluminescence from the measurement surface.

5. A fiber sensor comprising:

a first optical waveguide unit having a measurement surface formed at an end of an optical waveguide;

a detecting unit for detecting light information supplied from the measurement surface;

a second optical waveguide unit for transmitting light to the measurement surface; and a channel unit through which a specimen, serving as a measurement object to be measured by contact with the measurement surface, is caused to flow in and out via a specimen channel; wherein the optical waveguide is arranged in the first optical waveguide unit such that the measurement surface forms a part of a channel wall surface of the channel unit; and the optical information is provided by any of transmitted light, reflected light, and fluorescent light from the measurement surface.

6. The fiber sensor according to claim 1, wherein the optical waveguide unit and the channel unit are connected by means of a connector structure having a positioning pin so that the specimen channel is formed.

7. The fiber sensor according to claim 1, wherein the optical waveguide unit has a flow-in and flow-out channel formed therein, through which a specimen, serving as a measurement object, or a detergent is caused to flow in and out of the channel unit.

8. The fiber sensor according to claim 1, wherein the optical waveguide unit is provided with a capillary through which a specimen, serving as a measurement object, or a detergent is caused to flow in and out of the channel unit.

9. The fiber sensor according to claim 1, wherein a ligand layer is formed on the measurement surface in order that a specimen, serving as a measurement object, is supplied thereto.

10. The fiber sensor according to claim 1, wherein the measurement surface is formed by means of a plasmon resonance (SPR) sensor.

11. A fiber sensor apparatus comprising:

A fiber sensor comprising:

an optical waveguide unit having a measurement surface formed at an end of an optical waveguide; and a channel unit through which a specimen, serving as a measurement object to be measured by contact with the measurement surface, is caused to flow in and out via a specimen channel; wherein the optical waveguide is fixed to the optical waveguide unit such that the measurement surface forms a part of a channel wall surface of the channel unit; and the optical waveguide unit is arranged so as to be detachable from the channel unit;

at least one light source for supplying measuring light to be projected onto the measurement surface via the optical waveguide unit; and at least one light detecting unit for detecting light information supplied from the measurement surface.

12. The fiber sensor apparatus according to claim 11, wherein the light detecting unit includes switching means for switching the light information from the measurement surface in terms of time or space.

13. A fiber sensor apparatus comprising:

A fiber sensor comprising:

an optical waveguide unit having a measurement surface formed at an end of an optical waveguide; and a channel unit through which a specimen, serving as a measurement object to be measured by contact with the measurement surface, is caused to flow in and out via a specimen channel; wherein the optical waveguide is fixed to the optical waveguide unit such that the measurement surface forms a part of a channel wall surface of the channel unit; and the optical waveguide unit is arranged so as to be detachable from the channel unit;

at least one light source for supplying measuring light to be projected onto the measurement surface via the optical waveguide unit; and at least one light detecting unit for detecting light information supplied from the measurement surface;

wherein the light detecting unit includes switching means for switching the light information from the measurement surface in terms of time or space;

wherein the switching means includes a driving unit for rotating or moving one of more light shielding plates having one or more holes formed therein.

14. The fiber sensor apparatus according to claim 12, wherein the switching means performs the switching by time-dividing an electric signal supplied from the detecting unit.

15. The fiber sensor apparatus according to claim 12, wherein the switching is performed by time-dividing a light signal supplied to the detecting unit.

16. A measuring method for use in a fiber sensor apparatus, the measuring method comprising the steps of:

supplying light from a single light source to a plurality of optical waveguides;

concurrently projecting the light transmitted from the optical waveguides onto a plurality of measurement surfaces formed in a specimen channel;

switching, in terms of time or space, light information in any of transmitted light reflected light, and fluorescent light that is emitted from the light projected measurement surfaces; and detecting the switched light information by means of a single light detecting unit;

wherein the switching uses a driving unit for rotating or moving one or more light shielding plates having one or more holes formed therein.

* * * * *